United States Patent
McBride et al.

(10) Patent No.: US 6,296,752 B1
(45) Date of Patent: Oct. 2, 2001

(54) APPARATUS FOR SEPARATING MOLECULES

(75) Inventors: Sterling Eduard McBride, Lawrenceville; Satyam Choudary Cherukuri, Princeton; Rajan Kumar, Robbinsville; Judith Ann Ladd, Hamilton; Zhonghui Hugh Fan, Plainsboro; Bryan Lloyd Bentz, Princeton; Peter J. Zanzucchi, Lawrenceville, all of NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/326,139

(22) Filed: Jun. 4, 1999

Related U.S. Application Data

(60) Provisional application No. 60/088,297, filed on Jun. 5, 1998, provisional application No. 60/103,011, filed on Oct. 6, 1998, provisional application No. 60/093,222, filed on Jul. 17, 1998, and provisional application No. 60/097,335, filed on Aug. 19, 1998.

(51) Int. Cl.[7] .......................... G01N 27/26; G01N 24/447
(52) U.S. Cl. .......................... 204/547; 204/450; 204/456; 204/466; 204/600; 204/606; 204/616; 204/643
(58) Field of Search ................................... 204/450, 456, 204/466, 547, 600, 606, 616, 643

(56) References Cited

U.S. PATENT DOCUMENTS

| | | | |
|---|---|---|---|
| 4,390,403 | * | 6/1983 | Batchelder ............................ 204/547 |
| 5,569,367 | * | 10/1996 | Betts et al. ............................ 204/547 |
| 5,645,702 | * | 7/1997 | Witt et al. ......................... 204/600 X |
| 5,872,010 | | 2/1999 | Karger et al. ..................... 204/451 X |
| 5,964,997 | | 10/1999 | McBride et al. . |
| 6,113,768 | * | 9/2000 | Fuhr et al. ............................ 204/643 |

FOREIGN PATENT DOCUMENTS

| | | | |
|---|---|---|---|
| 2264783 | * | 8/1993 | (GB) . |
| WO 92/07657 | * | 5/1992 | (WO) . |
| WO 93/03850 | * | 3/1993 | (WO) . |

OTHER PUBLICATIONS

Duke and Austin, Microfabricated Sieve for the Continuous Sorting of Macromolecules, *Phys. Rev. Ltrs.*, vol. 80, No. 7, 1552–1555 (1998) No month available.

Ertas, Lateral Separation of Macromolecules and Polyelectrolytes in Microlithographic Arrays, *Phys. Rev. Ltrs.*, vol. 80, No. 7, 1548–1554 (1998) No month available.

Macka, et al., Changes in Electrolyte pH Due to Electrolysis during Capillary Zone Electrophoresis, *Anal. Chem.*, vol. 70, No. 4, 743–749 (1998) No month available.

Halsey, Electrorheological Fluids, *Science*, vol. 258, 761–766 (1992) No month available.

(List continued on next page.)

*Primary Examiner*—Jill Warden
*Assistant Examiner*—John S. Starsiak, Jr.
(74) *Attorney, Agent, or Firm*—William J. Burke

(57) ABSTRACT

Provided is an apparatus for separating, in a medium, a component from a composition comprising:

(1) an array of three or more electrodes arrayed along a pathway along which molecules of the composition are transported; and (2) a power source device for delivering to voltage to the electrodes; wherein the voltages delivered to the electrode array by the power source device are effective to:
  (a) alter the relative movement along the transport pathway of two or more of the molecules caused by a motive force, or
  (b) cause the molecules to move along the transport pathway.

19 Claims, 6 Drawing Sheets

OTHER PUBLICATIONS

Halsey and Martin, Electrorheological Fluids, *Science Am.*, 58–64 (1993) No month available.

Steding et al., Matrix–assisted laser Desorption Time–of–flight Mass Spectrometry of Oligonucleotides Using 3–Hydroxypicolonic Acid as an Ultraviolet–sensitive Matrix, *Rapid Commun., Mass Spectrometry*, vol. 7, 142–146 (1993) No month available.

* cited by examiner

APPARATUS FOR SEPARATING MOLECULES

This application claims the priority of U.S. Provisional Application 60/088,297, filed Jun. 5, 1998, U.S. Provisional Application 60/103,011, filed Oct. 6, 1998, U.S. Provisional Application 60/093,222, filed Jul. 17, 1998, and U.S. Provisional Application 60/097,335, filed Aug. 19, 1998.

The present invention relates to methods of and apparatuses for separating molecules, such as proteins or nucleic acids. The invention further relates to apparatuses that allow, and methods that use, an integrated mass spectrometric analysis.

SUMMARY OF THE INVENTION

Provided is an apparatus for separating, in a medium, a component from a composition comprising:

(1) an array of three or more electrodes arrayed along a pathway along which molecules of the composition are transported; and (2) a power source device for delivering to voltage to the electrodes; wherein the voltages delivered to the electrode array by the power source device are effective to:
  (a) alter the relative movement along the transport pathway of two or more of the molecules caused by a motive force, or
  (b) cause the molecules to move along the transport pathway.

The apparatus can further comprise: (3) where the electrode array and power source device do not provide a primary motive force for moving the molecules along the transport pathway, a source of motive force comprising (i) a source of pressure for promoting bulk fluid flow along the transport pathway or (ii) electrodes for promoting electrophoretic transport of the molecules along the transport pathway. In one embodiment, the three or more electrodes are separated from the fluid by a dielectric sufficient to prevent charge extraction or insertion from the electrodes to the fluid. In another embodiment, the three or more electrodes contact the fluid.

In an embodiment, the power source is programmed to deliver voltage to each of three or more said electrodes by periodically reversing the voltage polarity applied to the electrodes with a frequency of at least 10 Hz while maintaining a desired net effect. Preferably, the power source is programmed to deliver voltage to each of three or more said electrodes over an operating period of time encompassing at least one polarity cycle satisfying either (a) a first ratio of a voltage-integrated area $A_1$ associated with a first polarity to a voltage-integrated area $A_2$ associated with the other polarity or (b) a second ratio of a charge $q_1$ carried by the current associated with a first polarity to a charge $q_2$ carried by the current associated with the other polarity is less than 1: ½ and more than about ½:1.

In an embodiment, the apparatus has the three or more electrodes are located along one face of transport pathway, and the apparatus further comprises at least one counter electrode on another face of the transport pathway.

In an embodiment, the power source is programmed for delivering a traveling wave pattern of voltages to the electrodes, which traveling wave pattern of voltages is, in some embodiments, effective to move molecules in the fluid medium.

The invention provides a separation device comprising:

(1) an array of three or more first electrodes arrayed along a first pathway along which the molecules are transported; and (2) an array of three or more second electrodes arrayed along a second pathway, which diverges from the first pathway, along which the molecules are transported, wherein the first and second electrodes are effective to provide a motive force for moving molecules along the first or second pathway or for modifying the transport properties of molecules traveling along the first or second pathway.

The invention further provides a separation and analysis device comprising:

(1) a chamber formed between a first support and a second support, the chamber defining a region in which a separation medium can be placed, wherein the first support and second support can be separated;

(2) an array of three or more electrodes arrayed along a pathway found in the chamber, along which pathway the molecules are transported;

(3) a power source device for delivering to voltage patterns to the electrodes; and (4) a source of focused ionizing radiation adapted to be directed to a chamber surface of the first or second support when the first and second supports are separated.

Also provided is a method of separating a component from composition in an apparatus according to claim 1, the method comprising: moving the molecules under the power of the voltage applied to the electrodes. In one embodiment, the method comprises applying a traveling wave voltage pattern to the electrodes to move the molecules. In another embodiment the method comprises applying a motive force separate from said voltage driven electrodes to move the molecules; and altering the mobility of at least one component by applying voltage to said electrodes.

Further provided is a method of separating a component from composition and analyzing the component, the method comprising: separating the component by operating an apparatus of the invention; directing a source of ionizing radiation at the component in situ in the medium to generate ions from the component; and analyzing the component by mass spectroscopy.

Also provided is a method of separating a component from composition and analyzing the component, the method comprising: separating the component by operating an apparatus of the invention, wherein the apparatus is operated with a membrane adjacent to the counter-electrode(s) and to the medium; transferring in situ, under the influence of an electric field, the component to the membrane by operating the electrodes in conjunction with the counter-electrode(s); directing a source of ionizing radiation at the component in the membrane to generate ions from the component; and analyzing the component by mass spectroscopy.

DETAILED DESCRIPTION

Separation Apparatuses

Figure 1:
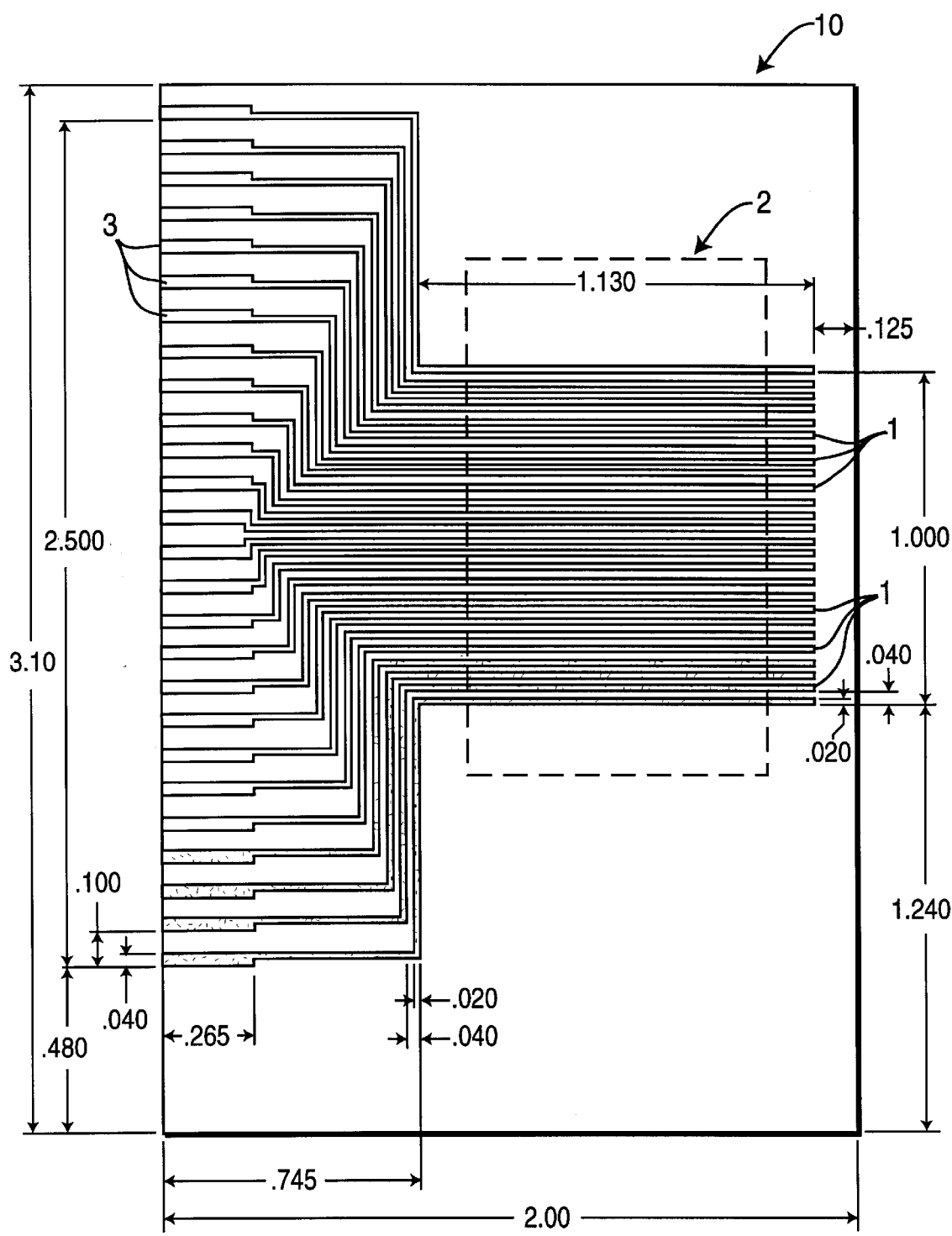
FIG. 1 displays an electrode-carrying plate viewed from above.

Provided are small-scaled devices for separating components such as molecules such as proteins, nucleic acids, other biopolymers, metabolites, and the like, from a composition. In preferred applications, such separations resolve two or more molecules. The devices include a number of electrodes, such as three, four, five, ten, twenty, forty, eighty or more, arrayed along the path along which separation shall proceed. In this regard, "path" encompasses the mix of specific pathways utilized certain separation procedures (as outlined below) in which the pathways of different molecules diverge. FIG. 1 illustrates a design for an electrode-carrying plate 10. The electrodes 1 sit, when fitted into a separation device, above or below an area 2 along which separation shall occur. The electrodes 1 are connected to leads 3 that allow the electrodes to be facilely connected to a device for providing power to the electrodes 1. The electrodes can, in some embodiments, contact the medium in which separation shall occur. The medium is (a) fluid, though components, including components for separation, can be suspended or (b) a fluid in a gel matrix. In other embodiments, a layer of non-conductive (i.e., dielectric) material intervenes to electrically isolate the electrodes from the medium.

The illustrated electrodes can be, for example, 0.5 mm in width, with a 0.5 mm separation between the electrodes. Or, the electrode density can be much higher, including for example, 1,000 electrodes per mm, such as a density from 0.4 to 10,000 electrodes per mm, or from 1 to 1000 electrodes per mm. Where the density increases, typically the dimensions of the region in which separations occur shall decrease, meaning that electronic field gradients acting on the medium can be effective with smaller voltages. Preferably, the separation path is 2.5 mm or less in length, more preferably, 0.1 mm or less in length, yet more preferably, 0.01 mm or less in length.

Figure 2A:
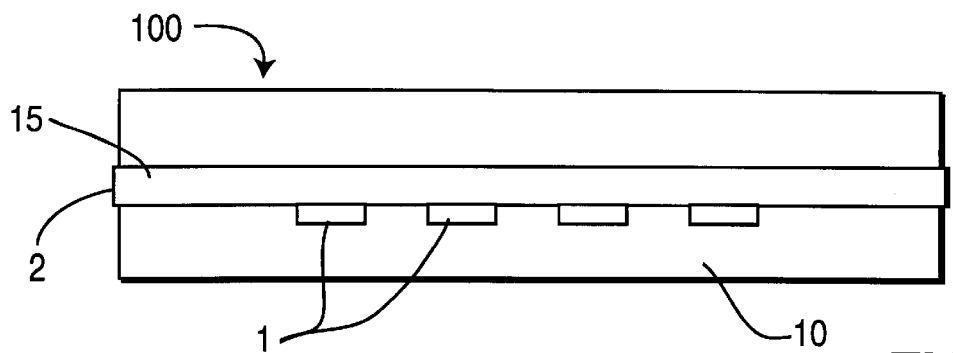
FIGS. 2A, 2B, 3A, 3B and 4 show separation apparatuses.
Figure 2B:
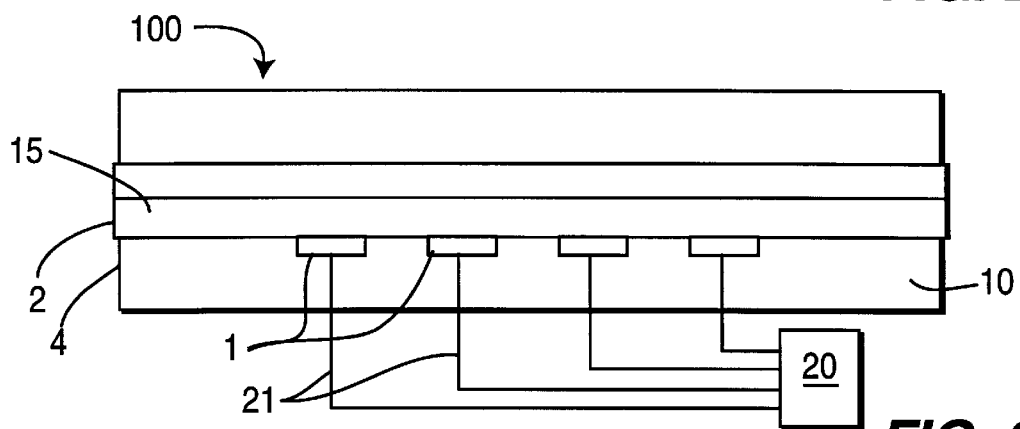
Figure 3A:
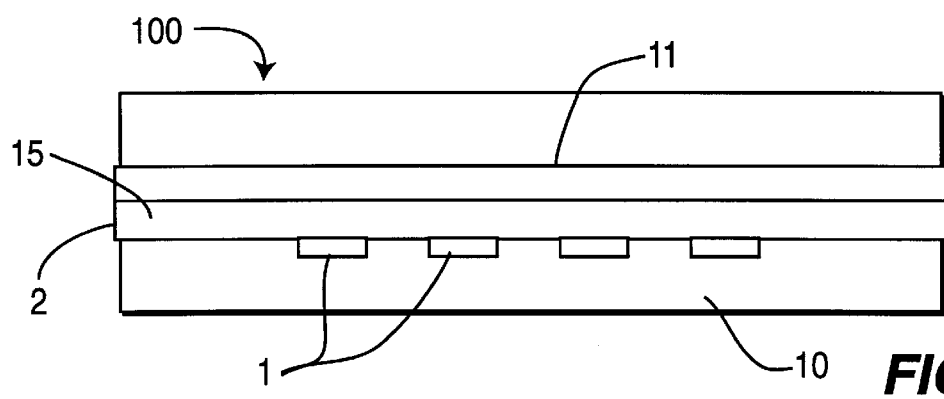
Figure 3B:
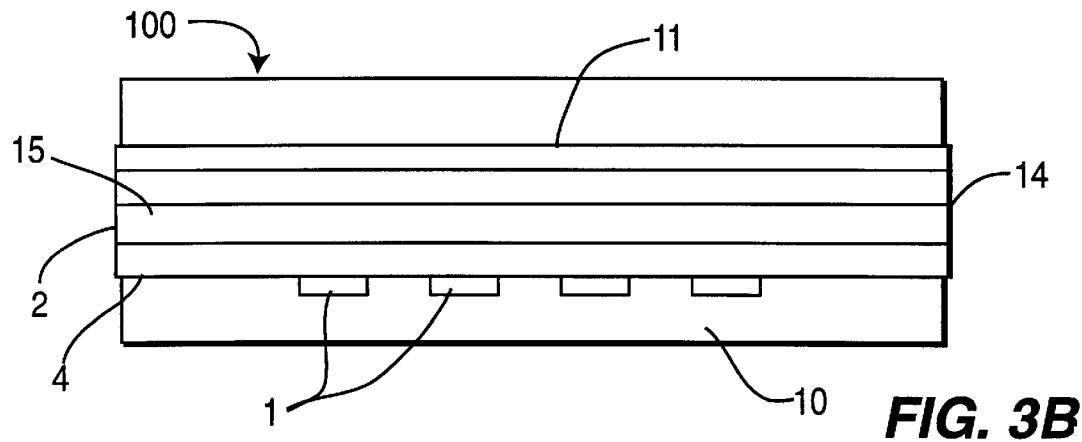

FIG. 2 illustrates, in cross-section, how the electrodes in a separation apparatus 100 can be arrayed relative to the separation area 2. In FIG. 2A, the electrodes 1 contact the medium 15 in the separation area; while in FIG. 2B, the electrodes 1 are isolated from the medium 15 by dielectric 4. FIG. 3A shows an embodiment in which the electrodes 1 can be operated with a counter-electrode 11. Such a counter-electrode can be operated, for example, at a set potential, such as a ground potential. It will be recognized that the counter-electrode can be segmented, i.e., made up of a number of individual electrodes which can be individually powered as appropriate. In FIG. 3B, the counter-electrode is isolated from the medium 15 by a second dielectric layer 14.

Figure 4:
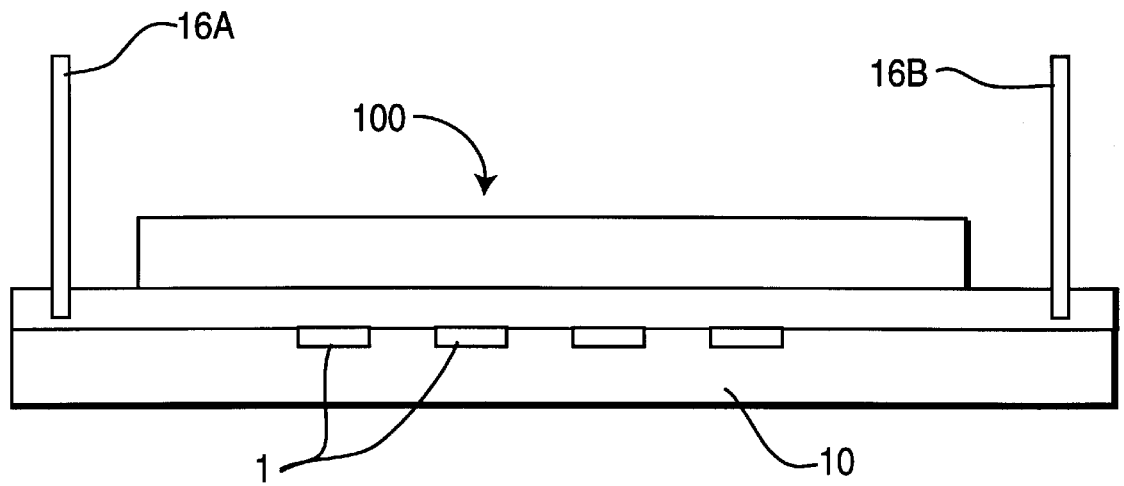

FIG. 4 illustrates an embodiment where the internal electrodes 1 are supplemented with additional electrodes, in this case first external electrode 16A and second external electrode 16B, which provide all or a substantial part of the field that moves the molecules. Electrodes 1 can serve to create changes that add to the molecular discrimination provided by the electrophoretic movement driven by first external electrode 16A and second external electrode 16B, as will be described below.

The electrode-carrying plate 10 can be constructed of a number of materials suitable for a given separation application. Typically, the electrodes are insulated from the bulk of the electrode-carrying plate 10, making it convenient for the plate to be formed of a dielectric material, such as glass, ceramic, plastic (such as Plexiglass™), silicone elastomer (Sylgard 184 by Coming), or a laminate. The electrodes are typically formed by a metallization process such as a thin or thick film deposition process. For example, a conductive ink, such as an ink containing gold particles, is applied to a substrate through a screen-printing process to create a positive image. The ink is dried, and then fired to densify the applied electrodes. In another example, the substrate is coated with photoresist and exposed, in a negative pattern, to UV light. The non-exposed photoresist, hence the photoresist that is not cross-linked, is removed to expose the substrate. The substrate is then coated, for example with a thin film of vacuum deposited metal, such as gold. Preliminary layers, which are preferably still thinner, can be applied to improve adhesion of the primary layer. For example, such preliminary layers can be formed with chromium or titanium containing gold. Plasma etch is used to remove areas containing photoresist. The electrode pattern can used as formed, or thickened or surface modified, for example by electroplating a metal such as chromium, gold, silver, platinum, palladium, nickel and the like. After metallization, the substrate is preferably cleaned by a process such as vapor phase degreasing.

If a gel is used as the medium, such a gel can be formed in several ways. For example, a mold can be formed around an electrode-carrying plate, and a pre-polymerized gel material poured into the mold using a doctor-blade to assure a flat surface (a doctor-blade is a device that presents at least one smooth edge or surface that is flat in at least one dimension, where the device is rounded about that edge or surface so that if the device is rotated against the mold edge, the flat edge is maintained). Such a pre-polymerized gel material can be, for example, a composition of monomers prior to polymerization, for example with light or another free-radical initiator, or a composition of polymers handled at a temperature above the gelling temperature of the polymers. In another illustrative method, the pre-polymerized gel material can be spin-coated within an appropriate mold, and then polymerized.

The gels can be formed with continuous or step-wise gradients having differing buffer, gel-forming polymer or cross-linker content, or gradients in some other property. Preferably, the gel is formed of polymer prepared by free-radical polymerization, such as polyacrylamide. Other materials, such as polyagarose, can be used. Typically, with a gel formed of monomer, the concentration of monomer is in the range of 5 to 25% wt/vol, preferably, 8 or 10% to 15%. A minor component of bivalent or multivalent monomer (i.e., cross-linker), as is known in the art, is used create a resilient gel; in some embodiments, the concentration of cross-linker is inversely proportional to the monomer concentration.

Figure 5:
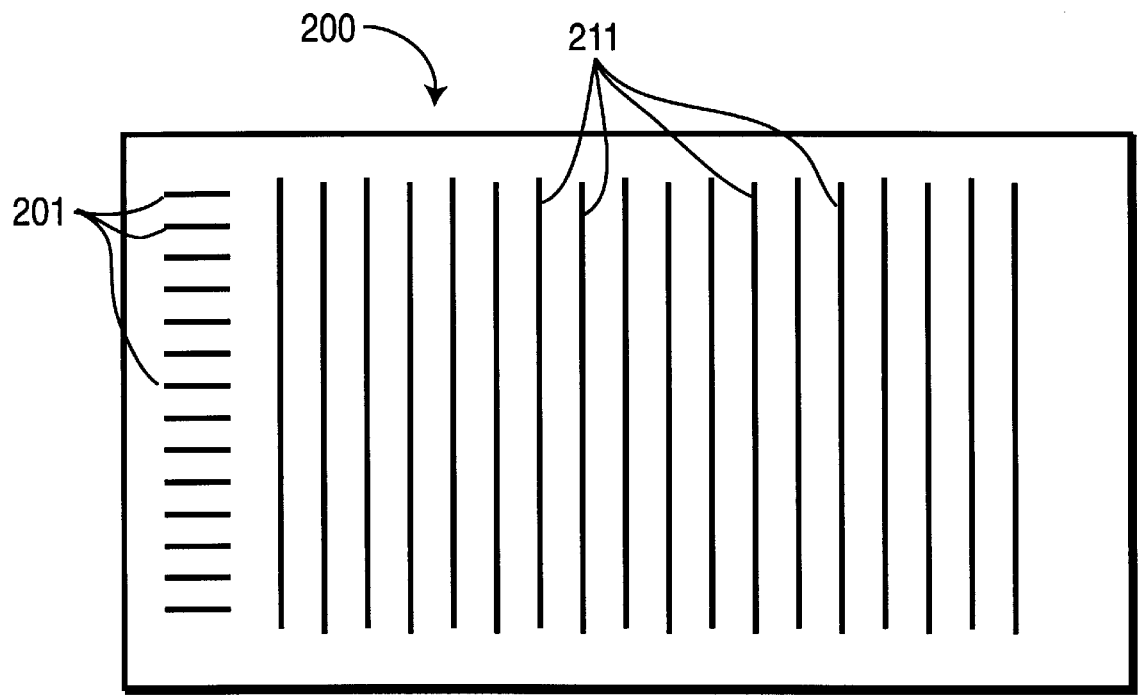
FIGS. 5, 6A and 6B show electrode-carrying plates viewed from above.

FIG. 5 illustrates an embodiment where an electrode-carrying plate 200 has first electrodes 201 and second electrodes 211. The first electrodes 201 can be used to apply a voltage protocol that moves molecules, for example, to apply sequentially greater voltage differences along the separation path to move a native or denatured molecule pursuant a size or $pK_a$ sensitive protocol. $pK_a$ sensitive protocols are often isoelectric focusing protocols that use ampholytes (zwitterionic species) that migrate in an electric field to establish a pH gradient such that molecules migrate to, and focus at, the region corresponding to the molecules' $pK_a$. Other protocols, such as those described herein, can be used. Certain of the first electrodes 201 can be used to provide a traditional electrophoretic field, for instance the two electrodes that are more towards the edges of the separation path, while the remaining first electrodes 201 can serve to modify the migration pattern of molecules. Note that these first electrodes 201, like second electrodes 211, can be accessed by voltage-supplying leads through conductive vias extending through the substrate that forms electrode-carrying plate 200. The second electrodes 211 correspondingly function to promote or modify a separation in a second a,-direction, the protocol for which is typically applied after the protocol for separation in the first direction. Such a device for two-dimensional separations can be operated correspondingly to the manner in which traditional devices are operated, which typically involves two distinct gel pouring steps to provide gels for the different separation processes. Alternatively, the operating protocols described below can allow a distinction in the separation protocols to be induced by the electrodes, thereby allowing the same separation medium to be used in both processes.

Where the internal electrodes contact the separation medium, they are preferably powered by a protocol that minimizes electrolysis-related bubbling. Such a protocol is described in U.S. Pat. No. 5,964,997. (U.S. application Ser. No. 08/821,480, filed Mar. 21, 1997), and involves applying voltage pulses, with a voltage that drives the desired effect applied at a greater amplitude but shorter duration than pulse of voltage of opposite polarity relative to a ground. Preferred parameters for such a protocol are described below.

Figure 6A:
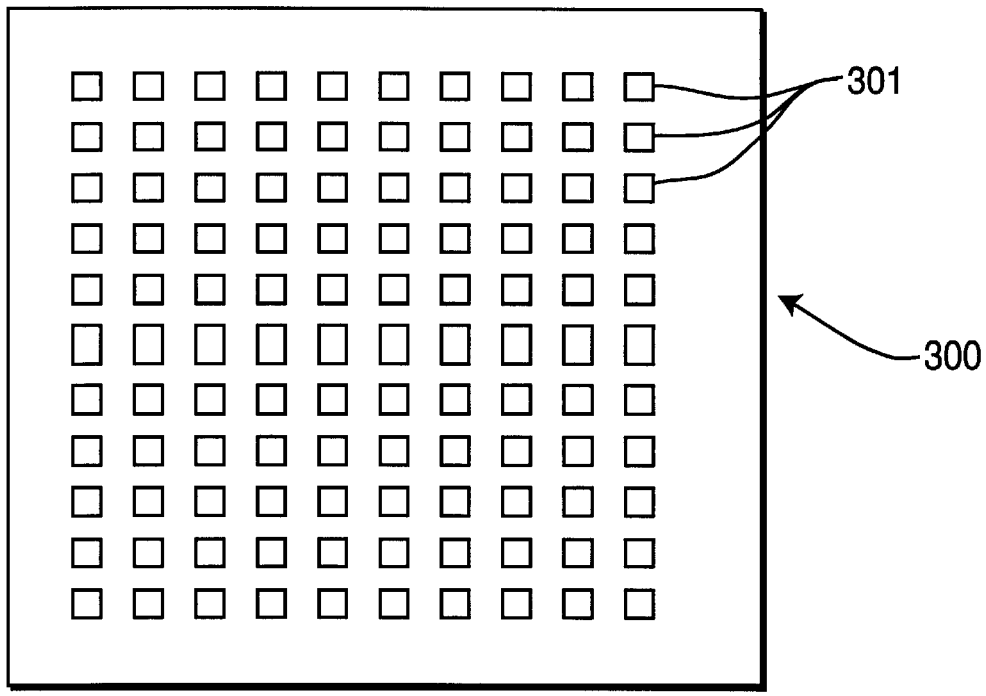
Figure 6B:
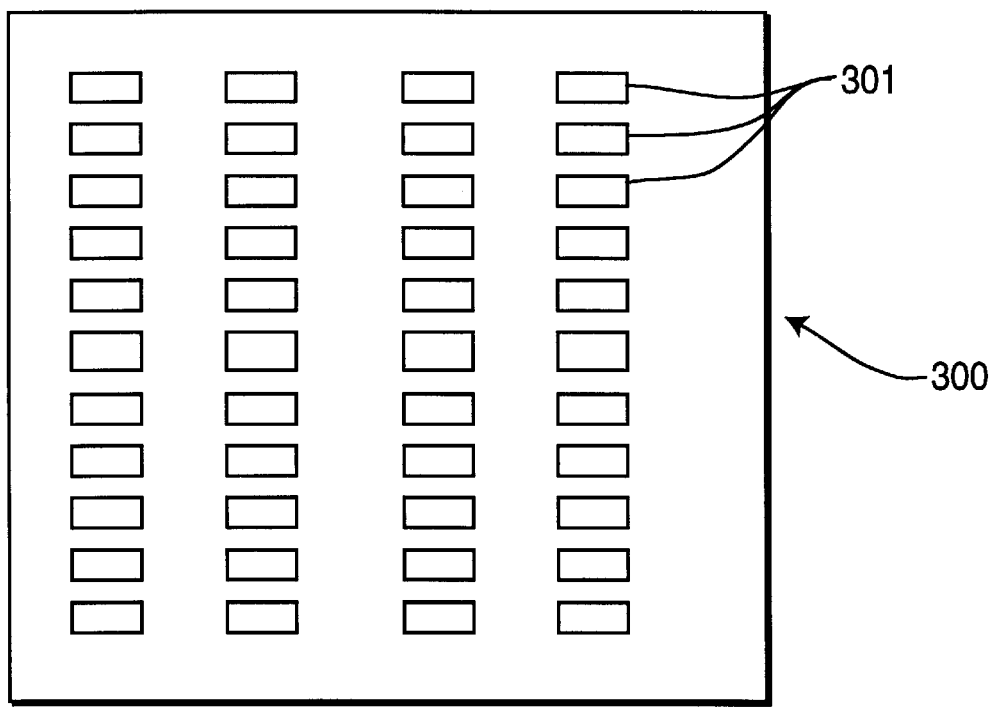
Figure 7:
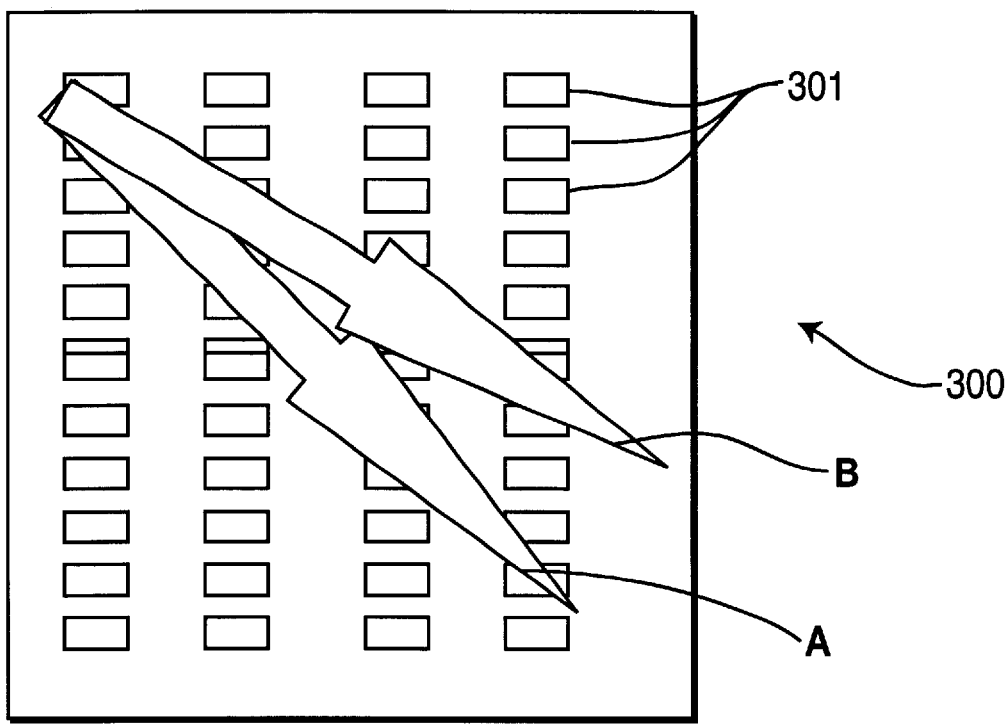
FIG. 7 illustrates the operation of a sieving method for separating components.

In another embodiment, an electrode-carrying plate 300 can contain a two-dimensional array of electrodes 301 of any number of shapes as illustrated in FIGS. 6A and 6B. Such a plate is particularly useful in providing electrically created asymmetrical barriers which act to change the probable specific path of a given molecule as indicated in FIG. 7, where molecule A proceeds by the primary path and molecule B proceeds by an altered path. The asymmetric barriers can be, for example, field-induced changes in pH or viscosity in the vicinity of the electrodes, or localized repulsive fields. The sieving phenomenon that creates selectivity by which differing molecules travel by differing paths is described, for the use of mechanical barriers, in Duke and Austin, *Phys Rev. Lirs.* 80: 1552–1555, 1998 and Ertas, *Phys. Rev. Ltrs.* 80: 1548–1554, 1998. The embodiment of electrode-carrying plate 300 can also be used to conduct two-dimensional separations using distinct protocols in each separation direction.

An electronic switching device can be incorporated into the separation device, such as into the electrode-carrying plate, to allow programmable control of individual electrodes.

Motive Force for Moving Molecules

The motive force can be provided by the internal electrodes, such as electrodes 1, which can be operated by a traveling wave protocol which moves the molecules, or pursuant to a protocol wherein each electrode has a successively larger or smaller voltage. Alternatively, the electrodes can provide a smaller to negligible part of the motive force, instead serving to provide bases for discrimination between molecules, as discussed below. Other motive forces can be additional electrodes (or subset of the internal electrodes) operating to provide the motive force. In some embodiments, the electrodes provide movement discrimination in the context of bulk liquid flow. Such bulk liquid flow can be gravity fed or driven by mechanical or other pumping devices. As has been described elsewhere, for example U.S. application Ser. No. 08/821,480, filed Mar. 21, 1997, U.S. application Ser. No. 08/744,386, filed Nov. 7, 1996, or U.S. application Ser. No. 08/998,406, filed Dec. 24, 1997, such pumping pressure can be provided with electrodes.

In certain embodiments, the invention provides means to separate molecules:

1) by using an electric field traveling wave to applied the force (F=qE) (electric Field traveling wave driven separation);

2) by using a pH traveling wave or static pH change induced by the electrodes (pH change found at the electrode interface) to add variability and programmability of the pH;

3) by using a viscosity traveling wave or viscosity static zones that are variable and programmable; or 4) by using both electric field traveling wave driven separation (that can include a pH traveling wave or static pH change) and viscosity zones (static or traveling).

The forces acting on a macromolecule or other molecule in an electric field can described as the force F=qE due to the field E as counterbalanced by the drag force. The mobility of a protein is given by:

$$\mu = \frac{q}{6\pi a\eta(1+a\kappa)} f(a\kappa)$$

$\mu$=mobility
q=charge
a=radius
$\eta$=shear viscosity
$k^{-1}$=Debye thickness
f(ak)=Henry's function Note that:
  The degree of ionization of the protein depends on the pH.
  Therefore, q depends on the pH, and q=0 at the isoelectric point of the protein.
  Accordingly, F (applied force) is different for different pH's even if the electric field E is the same.

Note further:
  Proteins with q≠0 will move along the direction of the traveling wave with different velocities depending on the charge of and the Electric field intensity E.
  Proteins at their isoelectric point (q=0) will not see a force. If we assume that the viscosity is constant all over the separation medium (buffer or gel):
  Charged proteins, whether negatively or positively charged, move by means of an electric field traveling wave in the direction of the traveling wave.

Figure 9:
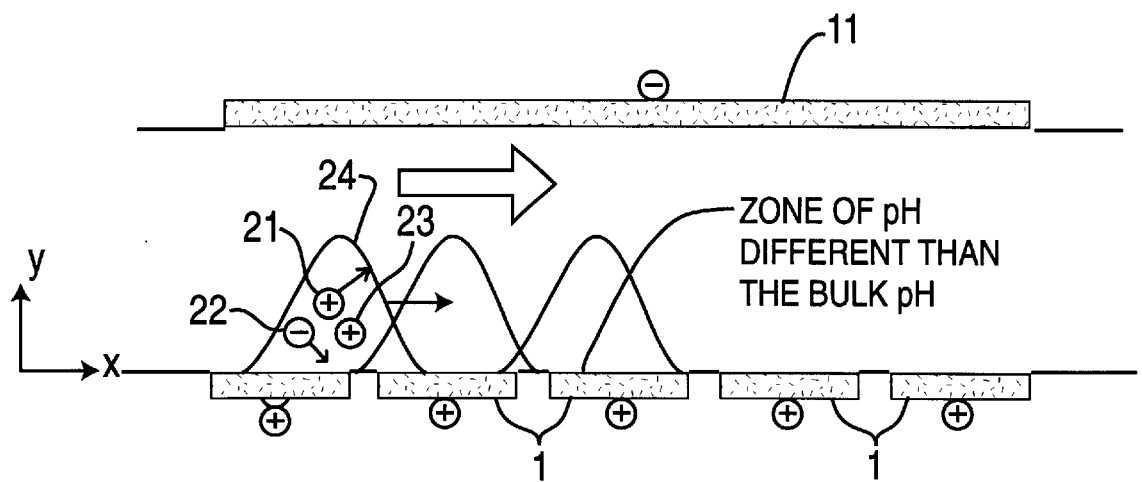
FIG. 9 illustrates the operation of a traveling wave.

FIG. 9 illustrates positive molecule 21 and negative molecule 22 affected by the adjacent electrode. Line 24 is illustrative of a prospective shape of the zone of influence of the field created by the electrode, though the line is illustrated as not traversing the medium purely for ease of illustration. Neutral molecule 23 is unaffected. A second effect is the generation of a pH traveling wave at the electrode interface that enhances separation and adds programmability. The pH can be affected by voltage, including a traveling wave of voltage applied to the electrodes. Electronically created pH changes are described, for example, *Anal. Chem.* 70: 743–749, 1998.

The viscosity of the separation medium can be also changed by applying an electric field. For example, consider electrorheological fluids engineered to transition to a solid. See, Halsey, *Science* 258: 761–766, 1992 or Halsey and Martin, *Scientific Am.* October 1993, pp. 58–64. Lessor changes in viscosity can be achieved from fluids containing molecules, particularly polymers, that are subject to a polarization induced by an electric field. Thus, the devices described here can generate a viscosity traveling wave. An electrophoretic force can be added by applying an electric field along the separation path. The viscosity created by the fields at electrodes 1 create a means for selecting molecules by enhancing the drag of larger, or more amorphously shaped molecules. Such induced viscosity can be moderated by the size of the electric field, allowing essentially a gradient gel to be applied without the complexity of pouring such a gel. This embodiment can be implemented with either viscosity traveling waves or static (localized) zones of modified viscosity.

Polymers and other materials which can be added to create an electrorheological effect include polystyrene, polytetrafluoroethylene (teflon), polyethylene, glass microspheres (micron and sub-micron sizes), and other materials in which charge polarization can be induced.

The electric field traveling waves and modified viscosity zones (either traveling waves or static zones) can be applied at the same time. The electric field traveling wave can include a pH traveling wave at the electrode interface. Separate subsets of the electrodes 1, for example alternating electrodes, can be used to implement the two effects.

The pH or viscosity mediation achieved by the present invention can be achieved through electrodes that directly contact the separation medium, or by induction.

Figure 10:
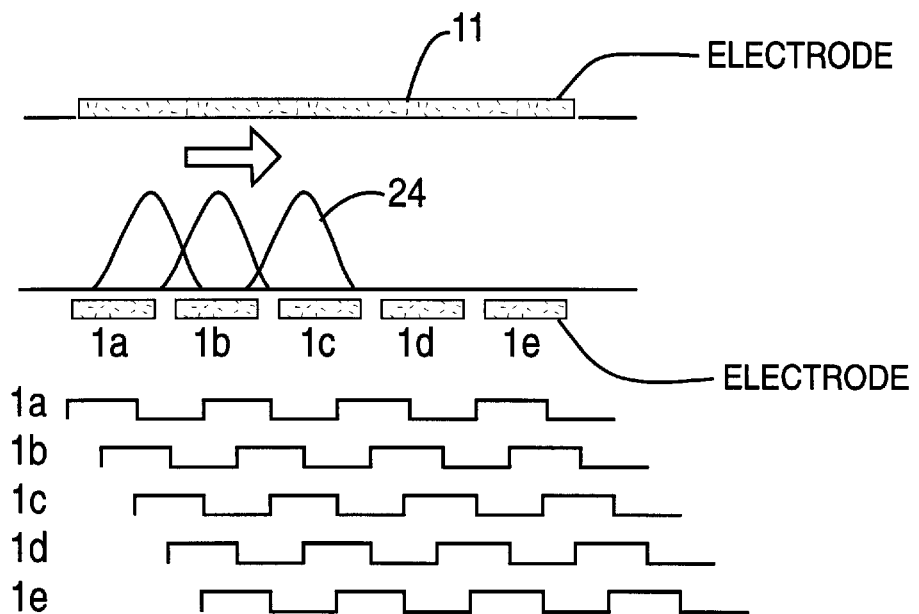
FIG. 10 illustrates a protocol for powering a traveling wave.

FIG. 10 illustrates a traveling wave protocol with five electrodes (1a through 1e). The lower part of the figure shows a timeline for the application block-shaped pulses of voltage. As will be recognized, more incremental changes in the applied voltage can also be used.

Integrated Mass Spectroscopy

Mass spectrometry has been used as a tool with gels for protein identification, quantification, and molecular weight (MW) calibration. The determination of protein MW on a 2-D gel using matrix-assisted laser desorption ionization mass spectroscopy (MALDI-MS) is often preceded by blotting protein spots to a membrane or by exciting spots from gel. MALDI-MS has been used for analysis of nucleic acid and identification of peptides, for instance in single neurons and cells.

The miniaturized separation devices of the present invention allow for the blotting step to be avoided, or for blotting to be incorporated into the device, allowing for automation. The separation medium or the transfer blot is treated with a chemical compound used to form a so-called matrix for MALDI, such as 3-hydroxypicolinic acid (See, Steding et al., *Rapid Commun. Mass Spectrom.* 7: 142–146, 1993). Where the separation medium is used directly to form the matrix, the width of the medium is preferably comparable to that of a membrane traditionally used in MALDI, or smaller. Such a medium can be selected to increase its efficiency for use in MALDI, such as for tolerance to the acid treatment, or for the presence of chromophores that assist energy transfer from the laser. A portion of the chip with separation medium or transfer membrane adherent, is then placed in the MALDI-MS unit, which consists of a laser (e.g., KrF excimer laser) and an ion-trap mass spectrometer. The laser used in matrix assisted laser desorption ionization is directed to particular regions to induce ionized molecules into the MS for analysis. By scanning, the entire transfer membrane or separation medium can be analized. Use of an ion trap mass spectrometer allows for collision induced dissociation of molecular (e.g., protein or nucleic acid) ions, which provides sequence information and aids in identification. Any mass spectrometry methodology that allows automated extraction of ions from the separation medium or transfer membrane, such as through the use of light energy or directed particles such as electrons, can be used. Other MS devices, such as time-of-flight devices can also be used.

By avoiding blotting, or blotting in an automated manner that avoids substantial manipulation of the materials, protein loses during blotting can be avoided or reduced.

In order to eliminate blotting step, the material of the separation medium used in the chip must meet these criteria: (1) be able to assist laser desorption ionization process, (2) be suitable for sealing with top layer, (3) and possesses negligible protein adsorption. The membrane can be, for example, formed of elastomers such as polydimethylsiloxane (PDMS), nitrocellulose or poly(vinylidene difluoride) (PVDF), or other polymers.

Figure 8:
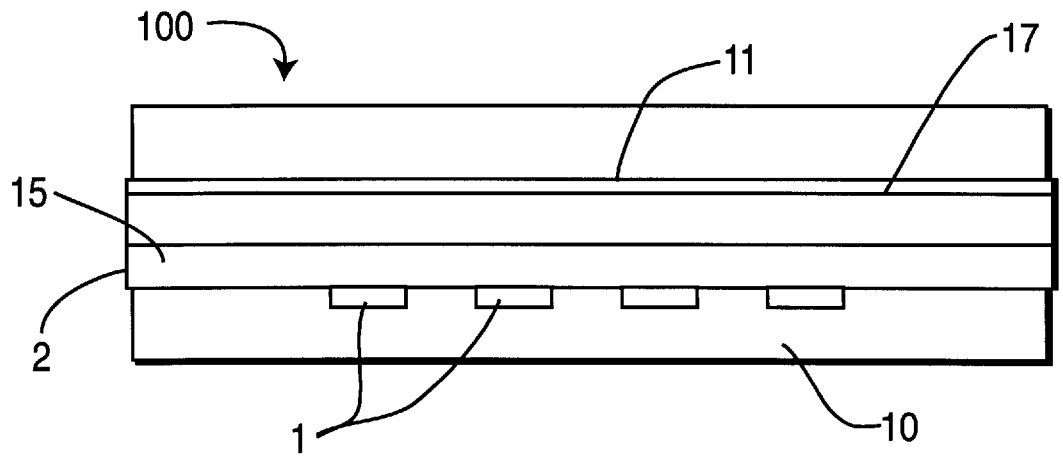
FIG. 8 shows a separation apparatus.

To illustrate how the blotting process can be integrated into the separation device, see FIG. 8. In the separation device of FIG. 8, a transfer membrane 17 is incorporated into the device. Following a separation procedure in which, for example, electrodes 1 participate to provide the motive power for separation or to provide a contribution to discriminating between molecules, the electrodes are used in conjunction with counter-electrode 11 to electro-blot molecules from the separation medium 15 to the transfer membrane 17. Bubble minimizing voltage protocols can be used to assure that such in situ transfer proceeds without disruption caused by bubbles.

Parameters for Limiting Bubbling

The polarity of the voltage used to obtain a desired result can be termed a "first polarity," while the opposite polarity can be termed a second polarity. Preferably, over an operating period of time encompassing at least one polarity cycle (as defined below) the voltage applied to an electrode can be characterized by either (a) a first ratio of a voltage-integrated area A, associated with a first polarity to a voltage-integrated area $A_2$ associated with the other polarity or (b) a second ratio of a charge $q_1$ carried by the current associated with a first polarity to a charge q2 carried by the current associated with the other polarity is between about 1: ½ and about ½:1. The voltage-integrated areas are the voltage profiles integrated over the relevant time period. More preferably, the first ratio or the second ratio is between about 1 : 0.8 and about 0.8: 1, yet more preferably the first or second ratio is between about 1: 0.9 and about 0.9: 1, still more preferably is between about 1: 0.95 and about 0.95: 1, yet still more preferably is between about 1: 0.98 and about 0.98: 1. In a highly preferred embodiment, the apparatus is operated pursuant to a control mechanism set such that one of these ratios is equal to one. Of course, the limitations of the control mechanism will imply some operational variance from this control target, but in this latter embodiment the effective ratio should remain within about 20% of 1.

Preferably, the frequency of a polarity cycle is at least about 10 Hz. Preferably, the frequency is from about 10 Hz to about 100 MHz, more preferably from about 100 Hz to about 10 kHz, yet more preferably from about 100 Hz to about 1 kHz. Preferably the maximum voltage applied of the first polarity is greater than the maximum voltage applied of the second polarity. Preferably, the maximum voltage of the second polarity is no more than about 50% of the maximum voltage of the first polarity, more preferably no more than about 40%, yet more preferably no more than about 30%.

Definitions

The following terms shall have, for the purposes of this application, the respective meaning set forth below.

electrorheological polymer. An electrorheological polymer is a polymer that responds to an electric field applied by the electrodes of the apparatus of the invention to change the local viscosity.

electrically isolate. Electrodes are electrically isolated from the separation medium if, assuming an aqueous medium, the intervening dielectric is sufficient to prevent substantial electrolysis. Substantial electrolysis is an amount which would have an impact on a separation procedure used with the separation device.

polarity cycle. A polarity cycle is the whole of (a) a continuous period operating with one of the polarities, and (b) an immediately following continuous period operating with the opposite polarity.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods can be used and that it is intended that the invention can be practiced otherwise than as specifically described herein. Accordingly, this invention includes all modifications encompassed within the spirit and scope of the invention as defined by the claims that follow.

What is claimed is:

1. An apparatus for separating, in a medium, a component from a composition comprising:
   (1) an array of three or more electrodes arrayed along a pathway along which molecules of the composition are transported, wherein the electrodes are arrayed to contact the medium; and
   (2) a power source device for delivering to voltage to the electrodes programmed such that the voltages delivered to the electrode array by the power source device are effective to:
      (a) alter the relative movement along the transport pathway of two or more of the molecules caused by a motive force, or
      (b) cause the molecules to move along the transport pathway;
   (3) a controller for operating the power source,
      wherein the power source is programmed to deliver voltage to each of three or more said electrodes by periodically reversing the voltage polarity applied to the electrodes with a frequency of at least 10 Hz while maintaining a desired net effect.

2. The apparatus of claim 1, further comprising:
   (4) where the electrode array and power source device do not provide a primary motive force for moving the molecules along the transport pathway, a source of motive force comprising (i) a pump for promoting bulk fluid flow along the transport pathway or (ii) electrodes for promoting electrophoretic transport of the molecules along the transport pathway.

3. The apparatus of claim 1, wherein the three or more electrodes are separated from the medium by a dielectric sufficient to prevent charge extraction or insertion from the electrodes to the fluid.

4. The apparatus of claim 1, wherein the power source is programmed to deliver voltage to each of three or more said electrodes over an operating period of time encompassing at least one polarity cycle satisfing either (a) a first ratio of a voltage-integrated area A1 associated with a first polarity to a voltage-integrated area A2 associated with the other polarity or (b) a second ratio of a charge q1 carried by the current associated with a first polarity to a charge q2 carried by the current associated with the other polarity is less than 1: ½ and more than about ½: 1.

5. The apparatus of claim 4, wherein power source is programmed such that the first ratio or the second ratio is between 1:0.8 and 0.8:1.

6. The apparatus of claim 1, wherein the three or more electrodes are located along one face of transport pathway, and the apparatus further comprises at least one counter electrode on another face of the transport pathway, wherein the space between the two faces defines the transport pathway.

7. The apparatus of claim 1, wherein the medium comprises at least one element selected from the group consisting of a gel and an electrorheological polymer.

8. The apparatus of claim 1, wherein the controller for the power source is programmed for delivering a traveling wave pattern of voltages to the electrodes.

9. The apparatus of claim 8, wherein the traveling wave pattern of voltages is effective to move molecules in the medium.

10. The apparatus of claim 1, wherein power source is programmed to deliver a pattern of polarity reversals and an associated voltage amplitude profile effective to reduce or eliminate nucleation of gas at the electrodes.

11. A method of separating a component from composition and analyzing the component, the method comprising:
   separating the component by delivering voltage to an array of three or more electrodes arrayed along a pathway along which molecules of the composition are transported in a medium, wherein the voltages delivered are effective to (a) alter the relative movement along the transport pathway of two or more of the molecules caused by a motive force, or (b) cause the molecules to move along the transport pathway;
   directing a source of ionizing radiation at the component in situ in the medium to generate ions from the component; and
   analyzing the component by mass spectroscopy.

12. A method of separating a component from composition and analyzing the component, the method comprising:
   separating the component by delivering voltage to an array of three or more electrodes arrayed along a pathway along which molecules of the composition are transported, wherein the voltages delivered are effective to (a) alter the relative movement along the transport pathway of two or more of the molecules caused by a motive force, or (b) cause the molecules to move along the transport pathway, wherein three or more electrodes are located along one face of transport pathway, and at least one additional electrode is located on another, second face of the transport pathway, wherein the space between the two faces defines the transport pathway;
   transferring in situ, under the influence of an electric field, the component to the membrane by operating the electrodes on one face of the pathway in conjunction with the electrode(s) on the second face;
   directing a source of ionizing radiation at the component in the membrane to generate ions from the component; and
   analyzing the component by mass spectroscopy.

13. A method of separating a component from composition and analyzing the component, the method comprising:
   providing an array of three or more electrodes arrayed along a pathway along which molecules of the composition are transported;

providing in the pathway a medium comprising an electrorheological polymer;

applying voltages to the electrodes to provide static or traveling wave zones of differential viscosity induced by resulting induced fields and the polymer; and moving one or more components of the composition along the pathway by electrophoresis or bulk flow.

14. The method of claim 13, wherein the one or more components are moved by electrophoreses primarily under the influence of electrodes separate from those creating the zones of differential viscosity.

15. The method of claim 14, wherein the voltages are applied to provide static zones.

16. The method of claim 14, wherein the voltages are applied to provide traveling wave zones.

17. The method of claim 14, wherein the voltages are applied to provide static zones.

18. The method of claim 14, wherein the voltages are applied to provide traveling wave zones.

19. The method of claim 13, wherein the one or more components are moved by bulk flow.

* * * * *